United States Patent [19]

Jaye et al.

[11] Patent Number: 4,868,113
[45] Date of Patent: Sep. 19, 1989

[54] RECOMBINANT DNA VECTOR ENCODING HUMAN ENDOTHELIAL CELL GROWTH FACTOR

[75] Inventors: Michael Jaye, Arlington, Va.; Wilson Burgess, Gaithersburg; Thomas Maciag, Rockville, both of Md.; William Drohan, Springfield, Va.

[73] Assignee: Rorer Biotechnology, Inc., King of Prussia, Pa.

[21] Appl. No.: 835,594

[22] Filed: Mar. 3, 1986

[51] Int. Cl.$^4$ .................. C12P 21/02; C12N 15/00; C12N 5/00; C12N 1/20; C12N 1/18; C12N 1/00; C07H 21/00

[52] U.S. Cl. .................. 435/70; 435/172.3; 435/240.2; 435/256; 435/320; 435/252.31; 435/252.33; 536/27; 935/11; 935/13

[58] Field of Search .................. 435/172.3, 70, 253, 435/320; 536/27; 935/11, 13

[56] References Cited

PUBLICATIONS de Ferra et al., Cell, vol. 43, pp. 721–727, Dec. 1985.
Lathe, J. Mol. Biol., vol. 183, pp. 1–12, (1985).
Hunkapiller et al., Methods in Enzymology, vol. 91, pp. 399–413 (1983).
Jaye et al., Nucleic Acids Research, vol. 11, pp. 2325–2335 (1983).
Maciag, T., "Angiogensis", Progress in Hemostasis and Thrombosis, vol. 7, pp. 167–182 (1984).
Maciag, T. et al., "Heparin Binds Endothelial Cell Growth Factor, the Principal Endothelial Cell Mitogen in Bovine Brain", Science, vol. 227, pp. 932–935 (1984).
Schreiber, A. B. et al., "Interaction of Endothelial Cell Growth Factor with Heparin: Characterization of Receptor and Antibody Recognition", Proc. Natl. Acad. Sci., vol. 82, pp. 6138–6142 (1985).
Burgess, W. H. et al., "Multiple Forms of Endothelial Cell Growth Factor", The Journal of Biological Chemistry, vol. 260, pp. 11389–11392 (1985).
Jaye, M. et al., "Modulation of the sis Gene Transcript During Endotheliel Cell Differentiation in Vitro", Science, vol. 228, pp. 882–885 (1985).
Conn, G. et al., "The Isolation and Purification of Two-Anionic Endothelial Cell Growth Factors from Human Brain", Biochemical and Biophysical Research Communications, vol. 124, pp. 262–268 (1984).

Primary Examiner—Alvin E. Tanenholtz

[57] ABSTRACT

Endothelial cell growth factor is achieved through the application of recombinant DNA technology to prepare cloning vehicles encoding the ECGF protein and procedures are disclosed for recovering ECGF protein essentially free of other proteins of human origin. The product is useful for, among other purposes, diagnostic applications and as potential in the treatment of damaged blood vessels or other endothelial cell-line structures.

22 Claims, 9 Drawing Sheets

```
                                                                    EcoRI                    -1
 Beta ECGF                         Acidic FGF       Alpha ECGF      GAATTCGGGAACGCGCCACAAGCAGCAGCTGCTGAGCC
 begins here                       begins here      begins here
 1                                      |               |                                                    120
ATGGCTGAAGGGGAAATCACCACCTTCACAGCCCTGACCGAGAAGTTTAATCTGCCTCCAGGGAATTACAAGAAGCCCAAACTCCTCTACTGTAGCAACGGGGGCCACTTCCTGAGGATC
M  A  E  G  E  I  T  T  F  T  A  L  T  E  K  F  N  L  P  P  G  N  Y  K  K  P  K  L  L  Y  C  S  N  G  G  H  F  L  R  I PstI                                                          240
CTTCCGGATGGCACAGTGGATGGGACAAGGGACAGGAGCGACCAGCACATTCAGCTGCAGCTCAGTGCGGAAAGCGTGGGGGAGGTGTATATAAAGAGTACCGAGACTGGCCAGTACTTG
L  P  D  G  T  V  D  G  T  R  D  R  S  D  Q  H  I  Q  L  Q  L  S  A  E  S  V  G  E  V  Y  I  K  S  T  E  T  G  Q  Y  L SphI       360
GCCATGGACACCGACGGGCTTTTATACGGCTCACAGACACCAAATGAGGAATGTTTGTTCCTGGAAAGGCTGGAGGAGAACCATTACAACACCTATATATCCAAGAAGCATGCAGAGAAG
A  M  D  T  D  G  L  L  Y  G  S  Q  T  P  N  E  E  C  L  F  L  E  R  L  E  E  N  H  Y  N  T  Y  I  S  K  K  H  A  E  K 480
AATTGGTTTGTTGGCCTCAAGAAGAATGGGAGCTGCAAACGCGGTCCTCGGACTCACTATGGCCAGAAAGCAATCTTGTTTCTCCCCCTGCCAGTCTCTTCTGATTAAAGAGATCTGTTC
N  W  F  V  G  L  K  K  N  G  S  C  K  R  G  P  R  T  H  Y  G  Q  K  A  I  L  F  L  P  L  P  V  S  S  D  trm 600
TGGTGTTGACCACTCCAGAGAAGTTTCGAGGGGTCCTCACCTGGTTGACCCCAAAAATGTTCCCTTGACCATTGGCTGCGCTAACCCCCAGCCCACAGAGCCTGAATTTGTAAGCAACTT
```

a. AcAlaGluGlyGluThrThrThrPheThrAlaLeuThrGluLysPheAsnLeuProLeuGlyAsnTyrLysLysPro b. (H₂N)-AsnTyrLysLysPro
                              5 a. LysLeuLeuTyrCysSerAsnGlyGlyTyrPheLeuArgIleLeuProAspGlyThrValAspGlyThrLysAspHis...
                10                  15              20              25              30 b. LysLeuLeuTyrCysSerAsnGlyGlyTyrPheLeuArgIleLeuProAspGlyThrValAspGlyThrLysAspHis...

c. AspThrAspGluLeuLeuTyrGlySerGlnThrProAsnGluGlu d. AspThrAspGluLeuLeuTyrGlySerGlnThrProAsnGluGlu

Hydrogen-Bonded Base Pairs

Fig. 4.

DESIGN OF AN OLIGONUCLEOTIDE PROBE FOR HUMAN ENDOTHELIAL CELL GROWTH FACTOR bovine ECGF protein sequence:    I    L    P    D    G    T    V    D    G    T    K degenerate coding sequence:

$$AT^A_T \quad CTX \quad CCX \quad GA^C_T \quad GGX \quad ACX \quad GTX \quad GA^C_T \quad GGX \quad ACX \quad AA^A_G$$
$$C \quad TT^A_G$$

$3 \times 6 \times 4 \times 2 \times 4 \times 4 \times 4 \times 2 \times 4 \times 2 \times 2 = 2.95 \times 10^5$ $$AT^A_T \quad CTX \quad CCX \quad GA^C_T \quad GGX \quad ACX \quad GTX \quad GA^C_T \quad GGX \quad ACX \quad AA^A_G$$
$$C \quad TT^A_G$$

CG dinucleotide:    not C or G        not C            not G
                                      or G
                      not C           not C $$AT^A_T \begin{smallmatrix}C\\G\\C^A_T\\T\end{smallmatrix} \begin{smallmatrix}A\\T^A_T\\T\end{smallmatrix} CC^A_T \quad GAT \quad GGX \quad AC^A_T \quad GTX \quad GA^C_T \quad GGX \quad ACX \quad AA^A_G$$

$3 \times 8 \times 2 \times 1 \times 4 \times 2 \times 4 \times 2 \times 4 \times 4 \times 2 = 9.84 \times 10^4$ codon usage:    ATT $^C_T$TT  CC$^A_T$  GAT  GGX  AC$^A_T$  GTX  GAT  GGX  AC$^A_T$  AAA
                                                                          C $1 \times 2 \times 2 \times 1 \times 4 \times 2 \times 4 \times 1 \times 4 \times 3 \times 1 = 1.54 \times 10^3$ allowance for inosine and G:T basepairs:    ATT  TTT  CCI  GAT  GGI  ACI  GTI  GAT  GGI  ACI  AAA

HOMOLOGY BETWEEN HUMAN ECGF cDNA SEQUENCE AND OLIGONUCLEOTIDE PROBES

```
a.      F   N   L   P   L   G   N   Y   K   K   P   K   L   L   Y   C   S   N   G   G   Y   F   L   R   I   L   P   D   G   T   V   D   G   T   K
b.                                                          AACTACAAAACCIAAACTICTITACTGCTCIAACGGIGGITACTTC      ATTTTCCIGATGGIACIGTIGATGGIACIAAA
        ::  ::::::  ::  ::  ::  :  ::::::  ::  ::::::                  ::/// ::: /::::: ::/::/:
c.      TTTAATCTGCCTCCAGGGAATTACAAGAAGCCCAAACTCCTCTACTGTAGCAACGGGGGCCACTTCCTGAGGATCCTTCCGGATGGCACAGTGGATGGGACAAGG
d.      F   N   L   P   L   G   N   Y   K   K   P   K   L   L   Y   C   S   N   G   G   Y   F   L   R   I   L   P   D   G   T   V   D   G   T   K
                                                            ECGF Oligonucleotide II*                            ECGF Oligonucleotide I a.      M   D   T   D   G   L   L   Y   G   S   Q   T   P   N   E   E
b.      ATGGACACIGACGGICTICTITACGGITCICAGACICCIAACGAGGAG
        ::::::::  ::::/::/  /::::  ::::::/::/::::/
c.      ATGGACACCGACGGGCTTTTATACGGCTCACAGACACCAAATGAGGAA
d.      M   D   T   D   G   L   L   Y   G   S   Q   T   P   N   E   E
        ECGF Oligonucleotide III*
``` a. Bovine ECGF protein sequence
b. Oligonucleotide probe
c. Human ECGF cDNA sequence
d. Human ECGF deduced amino acid sequence
: Signifies G:C or A:T base pairing
/ Signifies unusual base pairing
* Actual oligonucleotide used was the complement of the sequence shown

Fig. 7.

```
                                                                              EcoRI
                                                                         -1  GAATTCGGGAACGCGCCACAAGCAGCAGCTGCTGAGCC
                                    Acidic FGF          Alpha ECGF                                              120
                                    begins here         begins here
Beta ECGF                                    TTTAATCTGCCT CCAGGG AATTACAAGAAGCCCAAACTCCTCTACTGTAGCAACGGGGCCACTTCCTGAGGATC
begins here                                                                                                     240
ATGGCTGAAGGGGAAATCACCACCTTCACAGCCCTGACCGAGAAG F N L P P G N Y K K P K L L Y C S N G G H F L R I
M A E G E I T T F T A L T E K
                     PstI
CTTCCGGATGGCACAGTGGACGGGACAAGGAGACGACCAGCATTCAGTGCAGCTGCAGTCAGTGCGGAAAGCGTGGGAGGTGTATATAAAGAGTACCGAGACTGGCCAGTACTTG
L P D G T V D G T R D R S D Q H I Q L S A E S V G E V Y Y I K S T E T G Q Y L
                                                                                                        SphI
GCCATGGACACCGACGGGCTTTTATACGGCTCACAGACACCAAATGAGGAATGTTGTTCCTGGAAAGGCTGGAGGAGAACCATTACAACACCTATATCCAAGAAGCATGCAGAGAAG
A M D T D G L L Y G S Q T P N E E C L F L E R L E E N H Y N T Y I S K K H A E K  480
AATTGGTTTGTTGGCCTCAAGAAGAATGGGAGCTGCAAACGCGGTCCTGCAAATGGCCAAGAAAGCAATCTTGTTTCTCCCCCTGCCAGTCTCTTCTGATTAAAGAGATCTGTTC
N W F V G L K K N G S C K R G P R T H Y G Q K A I L F L P L P V S S D trm       600
TGGTGTTGACCACTCCAGAGAAGTTTCGAGGGGTCCTCACCTGTTGACCCCAAAAATGTTCCCTTGACCATTGGCTGCGCTAACCCCCAGCCCACAGAGCCTGAATTTGTAAGCAACTT
```

RECOMBINANT DNA VECTOR ENCODING HUMAN ENDOTHELIAL CELL GROWTH FACTOR

BACKGROUND OF THE INVENTION (1) Field Of The Invention

This invention relates to recombinant DNA-directed synthesis of certain proteins. More particularly, this invention relates to endothelial cell growth factor (ECGF), its recombinant DNA-directed synthesis, and ECGF's use in the treatment of endothelial cell damage and/or regeneration.

(2) The Prior Art

Endothelial cell growth factor, referred to herein as "ECGF", is a mitogen for endothelial cells in vitro. Growth of endothelial cells is a necessary step during the process of angiogenesis [Maciag, *Prog. Hemostasis and Thromb.*, 7:167-182 (1984); Maciag, T., Hoover, G. A., and Weinstein, R., *J. Biol. Chem.*, 257: 5333-5336 (1982)]. Bovine ECGF has been isolated by Maciag, et al., [*Science* 225:932-935 (1984)] using streptomycin sulfate precipitation, gel exclusion chromatography, ammonium sulfate precipitation and heparin-Sepharose affinity chromatography. Bovine ECGF purified in this manner yields a single-chain polypeptide which possesses an anionic isoelectric point and an apparent molecular weight of 20,000 [Maciag, supra; Schreiber, et al., *J. Cell Biol.*, 101:1623-1626 (1985); and Schreiber, et al., *Proc. Natl. Acad. Sci.*, 2:6138-6142 (1985)]. More recently, multiple forms of bovine ECGF have been isolated by Burgess, et al., [*J. Biol. Chem.* 260:11389-11392 (1985)] by sodium chloride gradient elution of bovine ECGF from the heparin-Sepharose column or by reversed-phase high pressure liquid chromatography (HPLC). The two isolated polypeptides, designated alpha- and beta-ECGF have apparent molecular weights of 17,000 and 20,000, respectively. Using this procedure, the bovine ECG contained in 8,500 ml of bovine brain extract ($6.25 \times 10^7$ total units) is concentrated into a total of 6 ml of alpha-ECGF ($3.0 \times 10^6$ units) and 3 ml of beta-ECGF ($5.2 \times 10^5$ units). This is a 9,300-fold purification of alpha-ECGF and 16,300-fold purification of beta-ECGF (Burgess, supra). Recently, murine monoclonal antibodies against bovine ECGF have been produced (Maciag, et al., supra) which may be useful in purifying bovine ECGF in a manner similar to the monoclonal antibody purification of Factor VIIIC described by Zimmerman and Fulcher in U.S. Pat. No. 4,361,509.

In general, recombinant DNA techniques are known. See *Methods In Enzymology*. (Academc Press, New York) volumes 65 and 68 (1979); 100 and 101 (1983) and the references cited therein, all of which are incorporated herein by reference. An extensive technical discussion embodying most commonly used recombinant DNA methodologies can be found in Maniatis, et al., *Molecular Cloning*, Cold Spring Harbor Laboratory (1982). Genes coding for various polypeptides may be cloned by incorporating a DNA fragment coding for the polypeptide in a recombinant DNA vehicle, e.g., bacterial or viral vectors, and transforming a suitable host. This host is typically an *Escherichia coli* (*E. coli*) strain, however, depending upon the desired product, eukaryotic hosts may be utilized. Clones incorporating the recombinant vectors are isolated and may be grown and used to produce the desired polypeptide on a large scale.

Several groups of workers have isolated mixtures of messenger RNA (mRNA) from eukaryotic cells and employed a series of enzymatic reactions to synthesize double-stranded DNA copies which are complementary to this mRNA mixture. In the first reaction, mRNA is transcribed into a single-stranded complementary DNA (cDNA) by an RNA-directed DNA poly-merase, also called reverse transcriptase. Reverse transcriptase synthesizes DNA in the 5'-3' direction, utilizes deoxyribonucleoside 5'-triphosphates as precursors, and requires both a template and a primer strand, the latter of which must have a free 3'-hydroxyl terminus. Reverse transcriptase products, whether partial or complete copies of the mRNA template, often possess short, partially double-stranded hairpins ("loops") at their 3' termini. In the second reaction, these "hairpin loops" can be exploited as primers for DNA polymerases. Preformed DNA is required both as a template and as a primer in the action of DNA polymerase. The DNA polymerase requires the presence of a DNA strand having a free 3'-hydroxyl group, to which new nucleotides are added to extend the chain in the 5'-3' direction. The products of such sequential reverse transcriptase and DNA polymerase reactions still possess a loop at one end. The apex of the loop or "fold-point" of the double-stranded DNA, which has thus been created, is substantially a single-strand segment. In the third reaction, this single-strand segment is cleaved with the single-strand specific nuclease Sl to generate a "blunt-end" duplex DNA segment. This general method is applicable to any mRNA mixture, and is described by Buell, et al., *J. Biol. Chem.*, 253:2483 (1978).

The resulting double-stranded cDNA mixture (ds-cDNA) is inserted into cloning vehicles by any one of many known techniques, depending at least in part on the particular vehicle used. Various insertion methods are discussed in considerable detail in *Methods In Enzymology*, 8:16-18 (1980), and the references cited therein.

Once the DNA segments are inserted, the cloning vehicle is used to transform a suitable host. These cloning vehicles usually impart an antibiotic resistance trait on the host. Such hosts are generally prokaryotic cells. At this point, only a few of the transformed or transfected hosts contain the desired cDNA. The sum of all transformed or transfected hosts constitutes a gene "library". The overall ds-cDNA library created by this method provides a representative sample of the coding information present in the mRNA mixture used as the starting material.

If an appropriate oligonucleotide sequence is available, it can be used to identify clones of interest in the following manner. Individual transformed or transfected cells are grown as colonies on a nitrocellulose filter paper. These colonies are lysed; the DNA released is bound tightly to the filter paper by heating. The filter paper is then incubated with a labeled oligonucleotide probe which is complementary to the structural gene of interest. The probe hybridizes with the cDNA for which it is complementary, and is identified by autoradiography. The corresponding clones are characterized in order to identify one or a combination of clones which contain all of the structural information for the desired protein. The nucleic acid sequence coding for the protein of interest is isolated and reinserted into an expression vector. The expression vector brings the cloned gene under the regulatory control of specific prokaryotic or eukaryotic control elements which allow the efficient expression (transcription and translation) of the ds-cDNA. Thus, this general technique is only applicable to those proteins for which at least a portion of their amino acid or DNA sequence is known for which an oligonucleotide probe is available. See, generally, Maniatis, et al., supra.

More recently, methods have been developed to identify specific clones by probing bacterial colonies or phage plaques with antibodies specific for the encoded protein of interest. This method can only be used with "expression vector" cloning vehicles since elaboration of the protein product is required. The structural gene is inserted into the vector adjacent to regulatory gene sequences that control expression of the protein. The cells are lysed, either by chemical methods or by a function supplied by the host cell or vector, and the protein is detected by a specific antibody and a detection system such as enzyme immunoassay. An example of this is the lambda gt$_{11}$ system described by Young and Davis, *Proc. Nat'l. Acad. Sci. USA*, 80:1194–1198 (1983) and Young and Davis, *Science*, 222:778 (1983).

SUMMARY OF THE INVENTION

The present invention has made it possible to provide readily available, large quantities of ECGF or ECGF fragments. This has been achieved with oligonucleotides whose design was based upon knowledge of the amino acid sequence of bovine ECGF and which react specifically with the ECGF cDNA. Production of ECGF is achieved through the application of recombinant DNA technology to prepare cloning vehicles encoding the ECGF protein and procedures for recovering ECGF protein essentially free of other proteins of human origin.

Accordingly, the present invention provides ECGF or its fragments essentially free of other proteins of human origin. ECGF is produced by recombinant DNA techniques in host cells or other self-replicating systems and is provided in essentially pure form. The invention further provides replicable expression vectors incorporating a DNA sequence encoding ECGF and a self-replicating host cell system transformed or transfected thereby. The host system is usually of prokaryotic, e.g., *E. coli* or *B. subtilis,* or eukaryotic cells.

The ECGF is produced by a process which comprises (a) preparing a replicable expression vector capable of expressing the DNA sequence encoding ECGF in a suitable host cell system; (b) transforming said host system to obtain a recombinant host system; (c) maintaining said recombinant host system under conditions permitting expression of said ECGF-encoding DNA sequence to produce ECGF protein; and (d) recovering said ECGF protein. Preferably, the ECGF-encoding replicable expression vector is made by preparing a ds-cDNA preparation representative of ECGF mRNA and incorporating the ds-cDNA into replicable expression vectors. The preferred mode of recovering ECGF comprises reacting the proteins expressed by the recombinant host system with a reagent composition comprising at least one binding step specific for ECGF. ECGF may be used as a therapeutic agent in the treatment of damaged or in regenerating blood vessels and other endothelial cell-lined structures.

BRIEF DESCRIPTION OF THE DRAWINGS

Line a: Amino-terminal amino acid sequence of bovine alpha ECGF.

Line b: Amino-terminal amino acid sequence of bovine beta ECGF. The portion in parenthesis corresponds to NH$_2$-terminal segment for which sequence could not be determined; amino acid composition is shown instead. The sequence beginning with PheAsnLeu . . . was determined from trypsin-cleaved bovine beta ECGF.

Line c: Amino acid sequence of cyanogen bromide-cleaved bovine alpha ECGF.

Line d: Amino acid sequence of cyanogen bromide-cleaved bovine beta ECGF.

FIG. 5 illustrates the design of an oligonucleotide probe for human Endothelial Cell Growth Factor.

Line a: Bovine trypsin- or cyanogen bromide-cleaved beta ECGF amino acid sequence.

Line b: Unique oligonucleotide probe.

Line c: Human ECGF cDNA sequence (determined from lambda ECGF clones 1 and 29).

Line d: Human ECGF amino acid sequence, deduced from cDNA sequence analysis.

FIG. 8 illustrates the complete cDNA sequence of human ECGF. The cDNA inserts from ECGF clones 1 and 29 were subcloned into M13mp18 and the ECGF-encoding open reading frame and flanking regions sequenced by the chain termination method. In frame stop codons at the 5' and 3' ends of the ECGF-encoding open reading frame are indicated by the underlined sequence and trm, respectively. The single-letter notation for amino acids is used: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; Y, Tyr.

FIG. 9 illustrates Northern blot analysis of ECGF mRNA. RNA was denatured in 2.2M formaldehyde and 50% formamide and fractionated by electrophoresis in a 1.25% agarose gel containing 2.2M formaldehyde. This was transferred to GeneScreen Plus (New England Nuclear) by blotting with 10X SSPE. Blots were hybridized to $^{32}$p-labeled nick-translated probes of ECGF clone 1 at 65° C. for 16 hours in a mixture containing 2X SSPE, 20X Denhardt's solution, yeast transfer RNA (200 ug/ml), and 0.2% SDS. The membrane was subsequently washed at 65° C., twice with 2X SSPE and 0.2% SDS, then twice with 0.2X SSPE and 0.2% SDS, air-dried, and exposed overnight to Kodak XAR film with an intensifying screen. The migration of 28S and 18S RNA is noted.

Lane 1: 10 ug human brain poly(A)-containing RNA.

Lane 2: 10 ug human adult liver poly(A)-containing RNA.

DESCRIPTION OF THE PREFERRED EMBODIMENTS

A. Introduction

As used herein, "ECGF" denotes endothelial cell growth factor or its fragments produced by cell or cell-free culture systems, in bioactive forms having the capacity to influence cellular growth, differentiation, and migration in vitro as does ECGF native to the human angiogenic process.

Different alleles of ECGF may exist in nature. These variations may be characterized by differences in the nucleotide sequence of the structural gene coding for proteins of identical biological function. It is possible to produce analogs having single or multiple amino acid substitutions, deletions, additions, or replacements. All such allelic variations, modifications, and analogs resulting in derivatives of ECGF which retain the biologically active properties of native ECGF are included within the scope of this invention.

"Expression vectors" refer to vectors which are capable of transcribing and translating DNA sequences contained therein, where such sequences are linked to other regulatory sequences capable of affecting their expression. These expression vectors must be replicable in the host organisms or systems either as episomes, bacteriophage, or as an integral part of the chromosomal DNA. One form of expression vector which is particularly suitable for use in the invention is the bacteriophage, viruses which normally inhabit and replicate in bacteria. Particularly desirable phage for this purpose are the lambda $gt_{10}$ and $gt_{11}$ phage described by Young and Davis, supra. Lambda $gt_{11}$ is a general recombinant DNA expression vector capable of producing polypeptides specified by the inserted DNA.

To minimize degradation, upon induction with a synthetic analogue of lactose (IPTG), foreign proteins or portions thereof are synthesized fused to the prokaryotic protein B-galactosidase. The use of host cells defective in protein degradation pathways may also increase the lifetime of novel proteins produced from the induced lambda $gt_{11}$ clones. Proper expression of foreign DNA in lambda $gt_{11}$ clones will depend upon the proper orientation and reading frame of the inserted DNA with respect to the B-galactosidase promoter and translation initiating codon.

Another form of expression vector useful in recombinant DNA techniques is the plasmid - a circular unintegrated (extra-chromosomal), double-stranded DNA loop. Any other form of expression vector which serves an equivalent function is suitable for use in the process of this invention.

Recombinant vectors and methodology disclosed herein are suitable for use in host cells covering a wide range of prokaryotic and eukaryotic organisms. Prokaryotic cells are preferred for the cloning of DNA sequences and in the construction of vectors. For example, E. coli K12 strain HB101 (ATCC No. 33694), is particularly useful. Of course, other microbial strains may be used. Vectors containing replication and control sequences which are derived from species compatible with the host cell or system are used in connection with these hosts. The vector ordinarily carries an origin of replication, as well as characteristics capable of providing phenotypic selection in transformed cells. For example, E. coli can be transformed using the vector pBR322, which contains genes for ampicillin and tetracycline resistance Bolivar, et al., Gene, 2:95 (1977)].

These antibiotic resistance genes provide a means of identifying transformed cells. The expression vector may also contain control elements which can be used for the expression of the gene of interest. Common prokaryotic control elements used for expression of foreign DNA sequences in E. coli include the promoters and regulatory sequences derived from the B-galactosidase and tryptophan (trp) operons of E. coli, as well as the pR and pL promoters of bacteriophage lambda. Combinations of these elements have also been used (e.g., TAC, which is a fusion of the trp promoter with the lactose operator). Other promoters have also been discovered and utilized, and details concerning their nucleotide sequences have been published enabling a skilled worker to combine and exploit them functionally.

In addition to prokaryotes, eukaryotic microbes, such as yeast cultures, may also be used. Saccharomyces cerevisiae, or common baker's yeast, is the most commonly used among eukaryotic microorganisms, although a number of other strains are commonly available. Yeast promoters suitable for the expression of foreign DNA sequences in yeast include the promoters for 3-phosphoglycerate kinase or other glycolytic enzymes. Suitable expression vectors may contain termination signals which provide for the polyadenylation and termination of the mRNA transcript of the cloned gene. Any vector containing a yeast-compatible promoter, origin of replication, and appropriate termination sequence is suitable for expression of ECGF.

Cell lines derived from multicellular organisms may also be used as hosts. In principle, any such cell culture is workable, whether from a vertebrate or invertebrate source. However, interest has been greatest in vertebrate cells, and propagation of vertebrate cells in culture (tissue culture) has become a routine procedure in recent years. Examples of such useful hosts are the VERO, HeLa, mouse C127, Chinese hamster ovary (CHO), WI38, BHK, COS-7, and MDCK cell lines. Expression vectors for such cells ordinarily include an origin of replication, a promoter located in front of the gene to be expressed, RNA splice sites (if necessary), and transcriptional termination sequences.

For use in mammalian cells, the control functions (promoters and enhancers) on the expression vectors are often provided by viral material. For example, commonly used promoters are derived from polyoma, Adenovirus 2, and most frequently, Simian Virus 40 (SV40). Eukaryotic promoters, such as the promoter of the murine metallothionein gene [Paulakis and Hamer, Proc. Natl. Acad. Sci. 80:397-401 (1983)], may also be used. Further, it is also possible, and often desirable, to utilize the promoter or control sequences which are naturally associated with the desired gene sequence, provided such control sequences are compatible with the host system. To increase the rate of transcription, eukaryotic enhancer sequences can also be added to the construction. These sequences can be obtained from a variety of animal cells or oncogenic retroviruses such as the mouse sarcoma virus.

An origin of replication may be provided either by construction of the vector to include an exogenous origin, such as that provided by SV40 or other viral sources, or may be provided by the host cell chromosomal replication mechanism. If the vector is integrated into the host cell chromosome, the latter is often sufficient.

Host cells can prepare ECGF which can be of a variety of chemical compositions. The protein is produced having methionine as its first amino acid. This methionine is present by virtue of the ATG start codon naturally existing at the origin of the structural gene or by being engineered before a segment of the structural gene. The protein may also be intracellularly or extracellularly cleaved, giving rise to the amino acid which is found naturally at the amino terminus of the protein. The protein may be produced together with either its own or a heterologous signal peptide, the signal polypeptide being specifically cleavable in an intra- or extracellular environment. Finally, ECGF may be produced by direct expression in mature form without the necessity of cleaving away any extraneous polypeptide.

Recombinant host cells refer to cells which have been transformed with vectors constructed using recombinant DNA techniques. As defined herein, ECGF is produced as a consequence of this transformation. ECGF or its fragments produced by such cells are referred to as "recombinant ECGF".

B. Recombinant and Screening Methodology

The procedures below are but some of a wide variety of well established procedures to produce specific reagents useful in the process of this invention. The general procedure for obtaining an mRNA mixture is to obtain a tissue sample or to culture cells producing the desired protein, and to extract the RNA by a process such as that disclosed by Chirgwin, et al., *Biochemistry*, 18:5294 (1979). The mRNA is enriched by poly(A)mRNA-containing material by chromatography on oligo (dT) cellulose or poly(U) Sepharose, followed by elution of the poly(A) containing mRNA fraction.

The above poly(A) containing mRNA-enriched fraction is used to synthesize a single-strand complementary cDNA (ss-cDNA) using reverse transcriptase. As a consequence of DNA synthesis, a hairpin loop is formed at the 3′ end of the DNA which will initiate second-strand DNA synthesis. Under appropriate conditions, this hairpin loop is used to effect synthesis of the ds-cDNA in the presence of DNA polymerase and using deoxyribonucleotide triphosphates.

The resultant ds-cDNA is inserted into the expression vector by any one of many known techniques. In general, methods can be found in Maniatis, et al., supra, and *Methods In Enzymology*, Volumes 65 and 68 (1980); and 100 and 101 (1983). In general, the vector is linearized by at least one restriction endonuclease, which will produce at least two blunt or cohesive ends. The ds-cDNA is ligated with or joined into the vector insertion site.

If prokaryotic cells or other cells which contain substantial cell wall material are employed, the most common method of transformation with the expression vector is calcium chloride pretreatment as described by Cohen, R.N., et al., *Proc. Nat'l. Acad. Sci. USA*, 69:2110 (1972). If cells without cell wall barriers are used as host cells, transfection is carried out by the calcium phosphate precipitation method described by Graham and Van der Eb, *Virology*, 52:456 (1973). Other methods for introducing DNA into cells such as nuclear injection, viral infection or protoplast fusion may be successfully used. The cells are then cultured on selective media, and proteins for which the expression vector encodes are produced.

Clones containing part or the entire cDNA for ECGF are identified with specific oligonucleotide probes deduced from a partial amino acid sequence determination of ECGF. This method of identification requires that the non-degenerate oligonucleotide probe be designed such that it specifically hybridizes to ECGF ds-cDNA. Clones containing ECGF cDNA sequences are isolated by radioactively labeling the oligonucleotide probe with $^{32}$P-ATP, hybridizing the radioactive oligonucleotide probe to the DNA of individual clones of a cDNA library containing ECGF-cDNA, and detection and isolation of the clones which hybridize by autoradiography. Such a cloning system is applicable to the lambda gt$_{11}$ system described by Young and Davis, supra.

Clones containing the entire sequence of ECGF are identified using as probe the cDNA insert of the ECGF recombinants isolated during the initial screening of the recombinant lambda gt$_{11}$ cDNA library with ECGF-specific oligonucleotides. Nucleotide sequencing techniques are used to determine the sequence of amino acids encoded by the cDNA fragments. This information may be used to determine the identity of the putative ECGF cDNA clones by comparison to the known amino acid sequence of the amino-terminus of bovine ECGF and of a peptide derived by cyanogen bromide cleavage of ECGF.

EXAMPLE

A. Preparation of Total RNA

Total RNA (messenger, ribosomal and transfer) was extracted from fresh two-day old human brain stem essentially as described by Chirgwin, supra, (1979). Cell pellets were homogenized in 5 volumes of a solution containing 4M guanidine thiocyanate, and 25 mM Antifoam A (Sigma Chemical Co., St. Louis, Mo.). The homogenate was centrifuged at 6,000 rpm in a Sorvall GSA rotor for 15 minutes at 10° C. The supernatant fluid was adjusted to pH 5.0 by addition of acetic acid and the RNA precipitated by 0.75 volumes of ethanol at −20° C. for two hours. RNA was collected by centrifugation and dissolved in 7.5M guanidine hydrochloride containing 2 mM sodium citrate and 5 mM dithiothreitol. Following two additional precipitations using 0.5 volumes of ethanol, the residual guanidine hydrochloride was extracted from the precipitate with absolute ethanol. RNA was dissolved in sterile water, insoluble material removed by centrifugation, and the pellets were re-extracted with water. The RNA was adjusted to 0.2M potassium acetate and precipitated by addition of 2.5 volumes of ethanol at −20° C. overnight.

B. Preparation of Poly(A)-containing RNA

The total RNA precipitate, prepared as described above, was dissolved in 20 mM Hepes buffer (pH 7.2) containing 10 mM EDTA and 1% SDS, heated at 65° C. for 10 minutes, then quickly cooled to 25° C. The RNA solution was then diluted with an equal volume of water, and NaCl was added to bring the final concentration to 300 mM NaCl. Samples containing up to 240 A$_{260}$ units of RNA were chromotagraphed on poly(U)-Sepharose using standard procedures. Poly(A)-containing RNA was eluted with 70% formamide containing 1 mM Hepes buffer (pH 7.2), and 2 mM EDTA. The eluate was adjusted to 0.24M NaCl and the RNA was precipitated by 2.5 volumes of ethanol at −20° C.

C. Construction of cDNA Clones in Lambda gt$_{11}$

Figure 1:
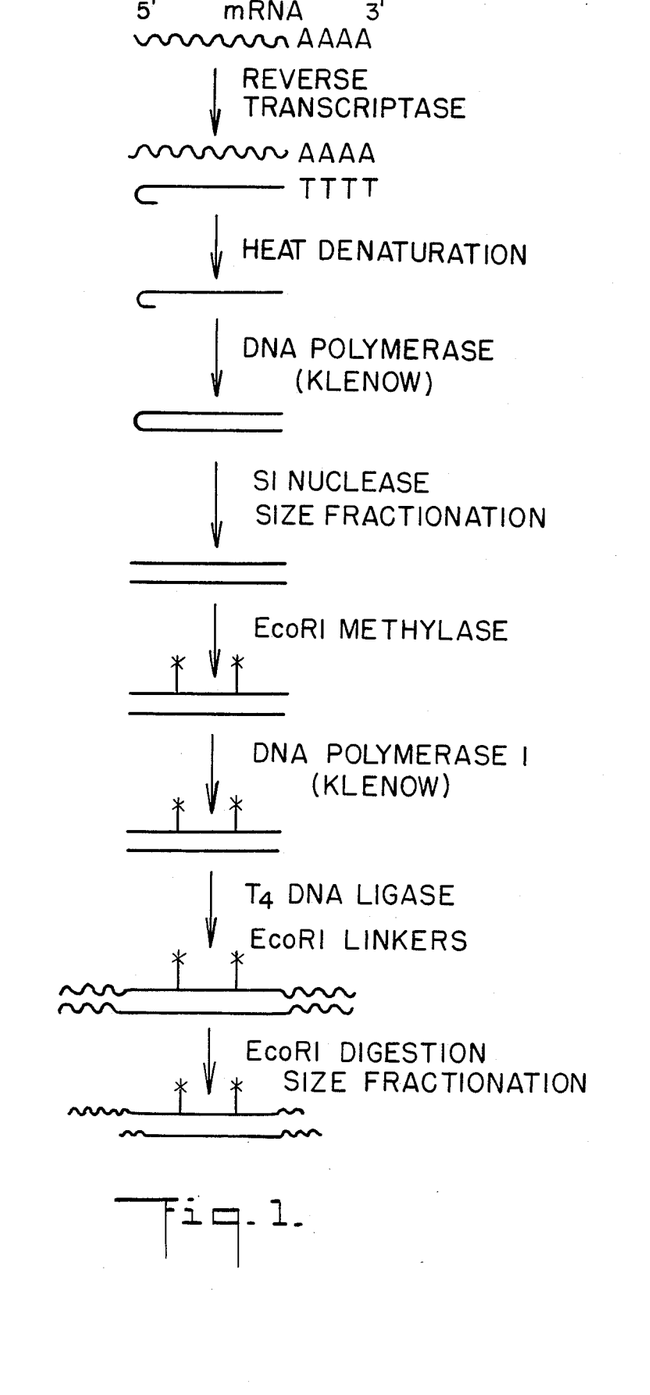
FIG. 1 illustrates a general procedure for enzymatic reactions to produce cDNA clones.

The procedure followed for the enzymatic reaction is shown in FIG. 1. The mRNA (20 μg) was copied into ds-cDNA with reverse transcriptase and DNA polymerase I exactly as described by Buell, et al., supra, and Wilkensen, et al., *J. Biol. Chem.*, 253:2483 (1978). The ds-cDNA was desalted on Sephadex G-50 and the void-volume fractions further purified on an Elutip-D column (Schleicher & Schuell, Keene, NH) following the manufacturer's directions. The ds-cDNA was made blunt-ended by incubation with S1 nuclease [Ricca, et al., *J. Biol. Chem.*, 256:10362 (1981)]. The reaction mixture consisted of 0.2M sodium acetate (pH 4.5), 0.4 M sodium chloride, 2.5 mM zinc acetate and 0.1 unit of S1 nuclease per ng of ds-cDNA, made to a final reaction volume of 100 μl. The ds-cDNA was incubated at 37° C. for one hour, extracted with phenol:chloroform, and then desalted on a Sephadex G-50 column as described above.

The ds-cDNA was then treated with EcoRI methylase and Klenow fragment of DNA polymerase I using reaction conditions described in Maniatis, et al., *Molecular Cloning*, supra. The cDNA was again desalted on Sephadex G-50 as described above and then ligated to 0.5 μg of phosphorylated EcoRI linkers using $T_4$ DNA ligase (Maniatis, et al., supra). The mixture was cleaved with EcoRI and fractionated on an 8% acrylamide gel in Tris-borate buffer (Maniatis, et al., supra). DNA with a size greater than 1 kilobase was eluted from the gel and recovered by binding to an Elutip-D column, eluted with 1M NaCl and then collected by ethanol precipitation.

Figure 2:
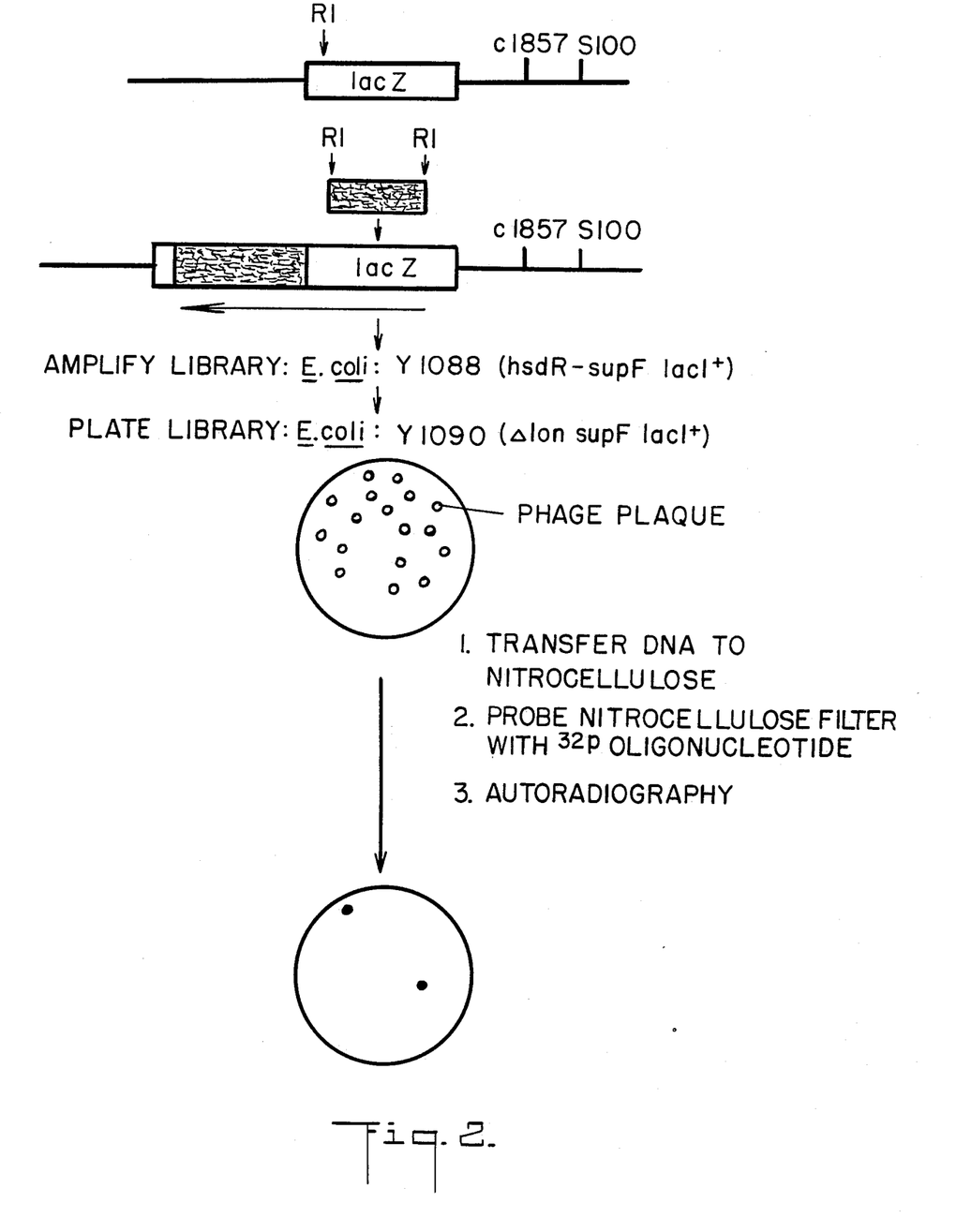
FIG. 2 illustrates the production of a library containing DNA fragments inserted into lambda gt$_{11}$.

As shown in FIG. 2, the DNA fragments were then inserted into EcoRI cleaved and phosphatase-treated lambda $gt_{11}$, using $T_4$ DNA ligase. A library of $5.7 \times 10^6$ phage was produced, of which approximately 65% were recombinant phage. The library was amplified by producing plate stocks at 42° C. on *E. coli* Y1088 [supE supF metB trpR hsdR− hsdM+ tonA21 strA lacU169 (proC.::Tn5) (pMC9)]. Amplification procedures are described in Maniatis, et al., supra. Important features of this strain, described by Young and Davis, supra, include (1) supF (required suppression of the phage amber mutation in the S gene), (2) hsdR− hsdM+ (necessary to prevent restriction of foreign DNA prior to host modification), and (3) lacU169 (proC.::Tn5), and (4) (pMC9) (a lac I-bearing pBR322 derivative which represses, in the absence of an inducer, the expression of foreign genes that may be detrimental to phage and/or cell growth).

D. Identification of Clones Containing ECGF Sequence

To screen the library for recombinant phage containing ECGF cDNA, $1.5 \times 10^6$ phage were plated on a lawn of *E. coli* Y1090 [ΔlacU169 proAΔ lon araD139 strA supF (trpC22::Tn10) (pMC9)] and incubated at 42° C. for 6 hours. After the plates were refrigerated overnight, a nitrocellulose filter was overlaid on the plates. The position of the filter was marked with a needle. The filter removed after one minute and left to dry at room temperature. From each plate, a duplicate filter was prepared exactly as described, except that the filter was left in contact with the plate for 5 minutes. All filters were then prepared for hybridization, as described in Maniatis, et al., supra. This involved DNA denaturation in 0.5M NaOH, 1.5M NaCl, neutralization in 1M Tris-HCl, pH 7.5, 1.5M NaCl, and heating of the filters for 2 hours at 80° C. in vacuo.

Figure 3:
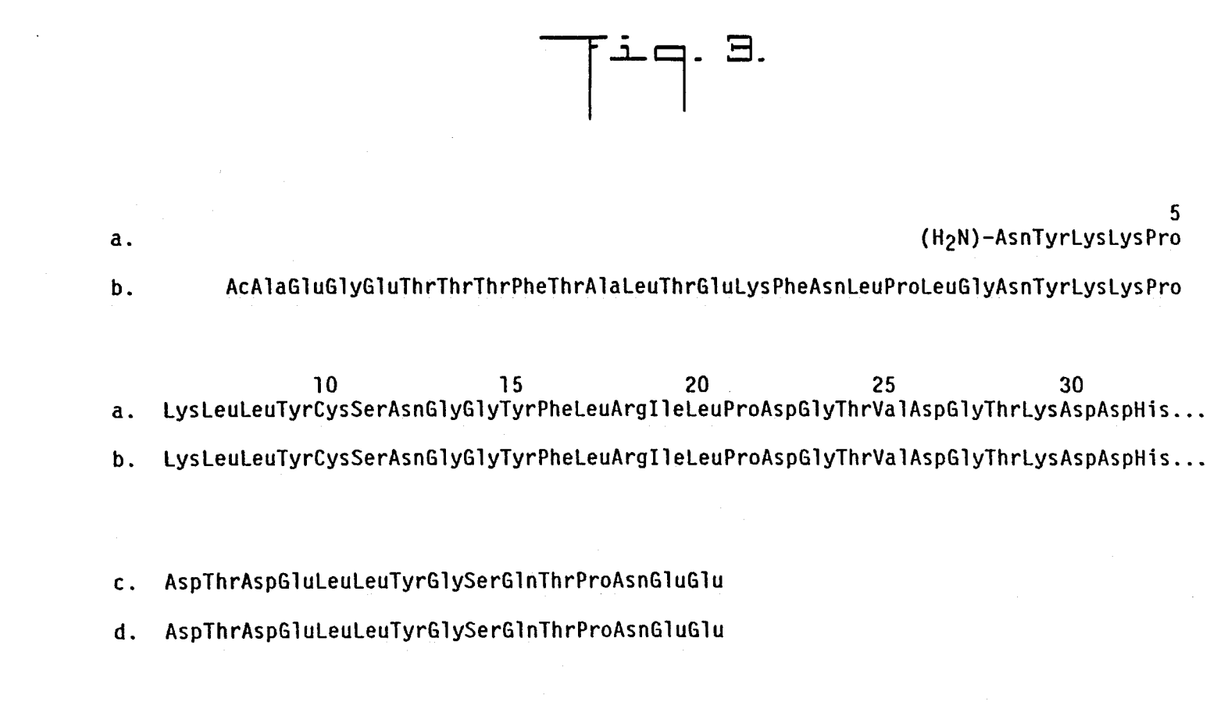
FIG. 3 illustrates a partial amino acid sequence of bovine alpha and beta ECGF.

To screen the human brain stem cDNA library for clones containing ECGF inserts, a specific oligonucleotide was designed. This oligonucleotide was based upon a partial amino acid sequence analysis of the amino terminus of ECGF. As shown in FIG. 3, lines a & b, bovine ECGF is isolated as two species, designated alpha and beta ECGF, which differ only in the amino acids found at the respective amino termini. As shown in FIG. 3, line b, beta-ECGF is a slightly larger species than alpha-ECGF. The exact amino acid sequence at the amino terminus of beta-ECGF is undetermined, however, a sequence derived from fast atom bombardment mass spectral analysis and the amino acid composition of the amino terminal tryptic peptide of bovine beta-ECGF is shown. The amino terminal blocking group appears to be acetyl. If intact beta-ECGF is cleaved by trypsin, a second amino acid sequence found in beta but not alpha ACGF starting with PheAsnLeu . . . is determined. This sequence is also found at the amino terminus of acidic fibroblast growth factor [Thomas, K.A. et al., *Prac. Natl. Acad. Sci.*, 82:6409–6413 (1985)]. The amino terminus of alpha-ECGF s AsnTyrLys . . . (FIG. 3, line a) and is the equivalent of beta-ECGF minus an amino terminal extension. In FIG. 3, lines c and d set forth for comparison the amino acid sequence of cyanogen bromide-cleaved bovine alpha and beta ECGF, respectively.

Figure 4:
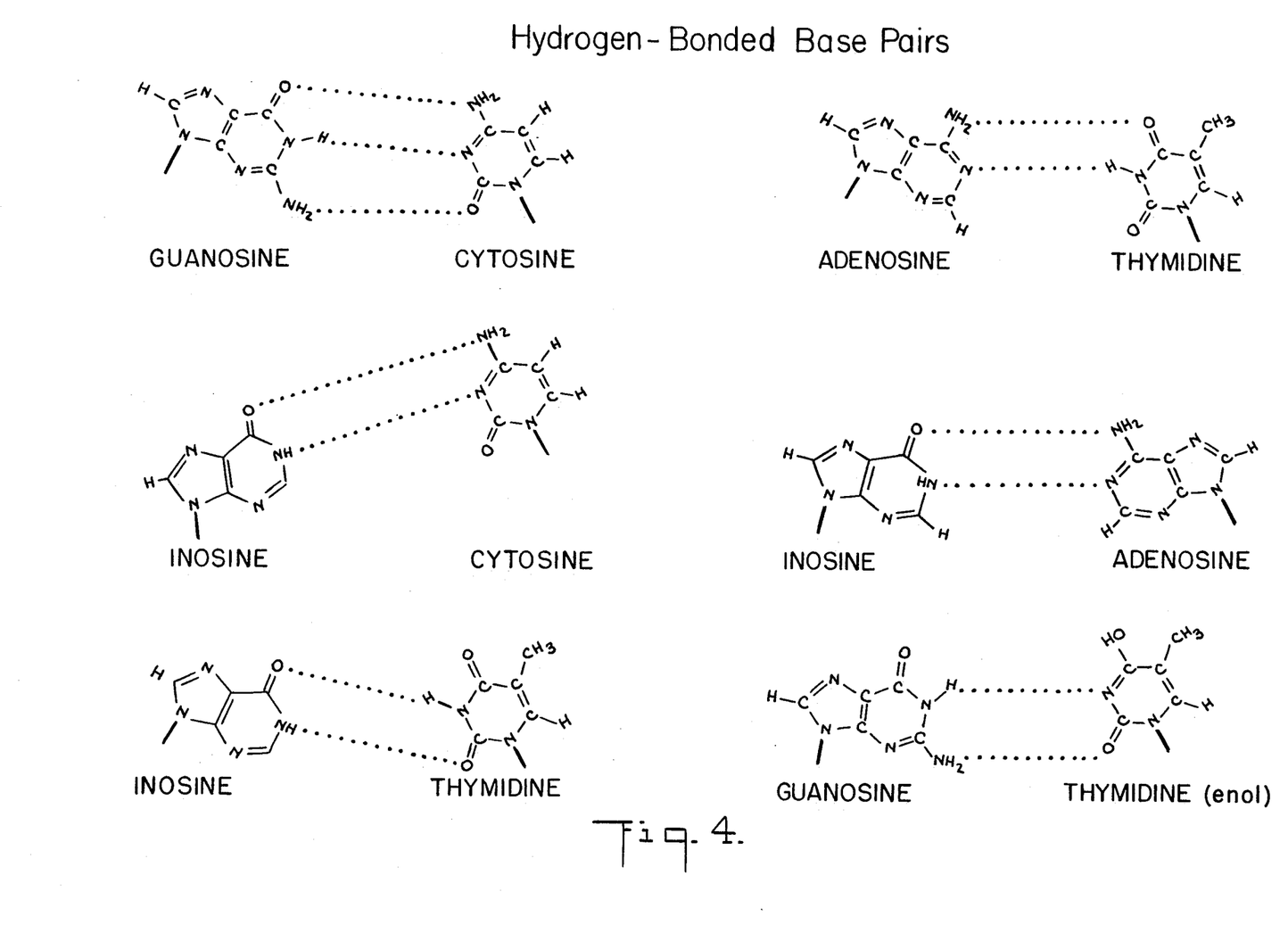
FIG. 4 illustrates hydrogen-bonded base pairs.

For oligonucleotide design, the amino acid sequence IleLeuProAspGlyThrValAspGlyThrLys, corresponding to alpha-ECGF amino acids 19–29 inclusive, was chosen. Rather then design a mixture of oligonucleotides covering all of the possible coding sequences (owing to the degeneracy of the genetic code), a long unique oligonucleotide was designed. Such oligonucleotide probes have been previously shown to be successful probes in screening complex cDNA [Jaye, et al., *Nucleic Acids Research* 11:2325–2335, (1983)] and genomic [Gitschier, et al., *Nature*, 312:326–330 (1984)] libraries. Three criteria were used in designing the ECGF probe: (1) The dinucleotide CG was avoided. This strategy was based upon the observed under representation of the CG dinucleotide in eukaryotic DNA [Josse, et al., *J. Biol. Chem.* 236:864–875, (1961)]; (2) preferred codon utilization data was used wherever possible. A recent and comprehensive analysis of human codon utilization was found in Lathe, *J. Mol. Biol.* 183:1–12 (1985); and (3) wherever the strategies of CG dinucleotide and preferred codon utilization were uninformative, unusual base pairing was allowed. This strategy was based upon the natural occurrence of G:T, I:T, I:A and I:C base pairs which occur in the interaction between tRNA anticodons and mRNA codons [Crick, *J. Mol. Biol.* 19:548–555, (1966)]. A diagram of usual and unusual base pairs is shown in FIG. 4. Use of I (Inosine) in a hybridization probe was first demonstrated, in a model experiment, by Ohtsuka, et al., *J. Biol. Chem.* 260:2605–2608 (1985). The overall strategy and choice made in the design of the oligonucleotide used to screen the human brain stem cDNA library for ECGF is shown in FIG. 5. In addition, two other oligonucleotides, designed with the same strategy, were constructed.

Approximately 30 pmole of the oligonucleotide shown in FIG. 5 were radioactively labeled by incubation with $^{32}$P-gamma-ATP and T4 polynucleotide kinase, essentially as described by Maniatis, et al., supra. Nitrocellulose filters, prepared as described above, were prehybridized at 42° C. in 6X SSPE (1X SSPE=0.18M NaCl, 0.01M NaHPO$_4$ pH 7.2, 0.001M EDTA), 2X Denhardt's (1X Denhardt's - 0.02% each Ficoll, polyvinylpyrrolidone, bovine serum albumin), 5% dextran sulfate, and 100 μg/ml denatured salmon sperm DNA. The 32P-labeled oligonucleotide was added following four ours of prehybridization, and hybridization continued overnight at 42° C. Unhybridized probe was removed by sequential washing at 37° C. in 2X SSPE, 0.1% SDS.

From $1.5 \times 10^6$ plaques screened, 2 plaques gave positive autoradiographic signals after overnight exposure. These clones were purified to homogeneity by repeated cycles of purification using the above oligonucleotide as hybridization probe.

Figure 6:
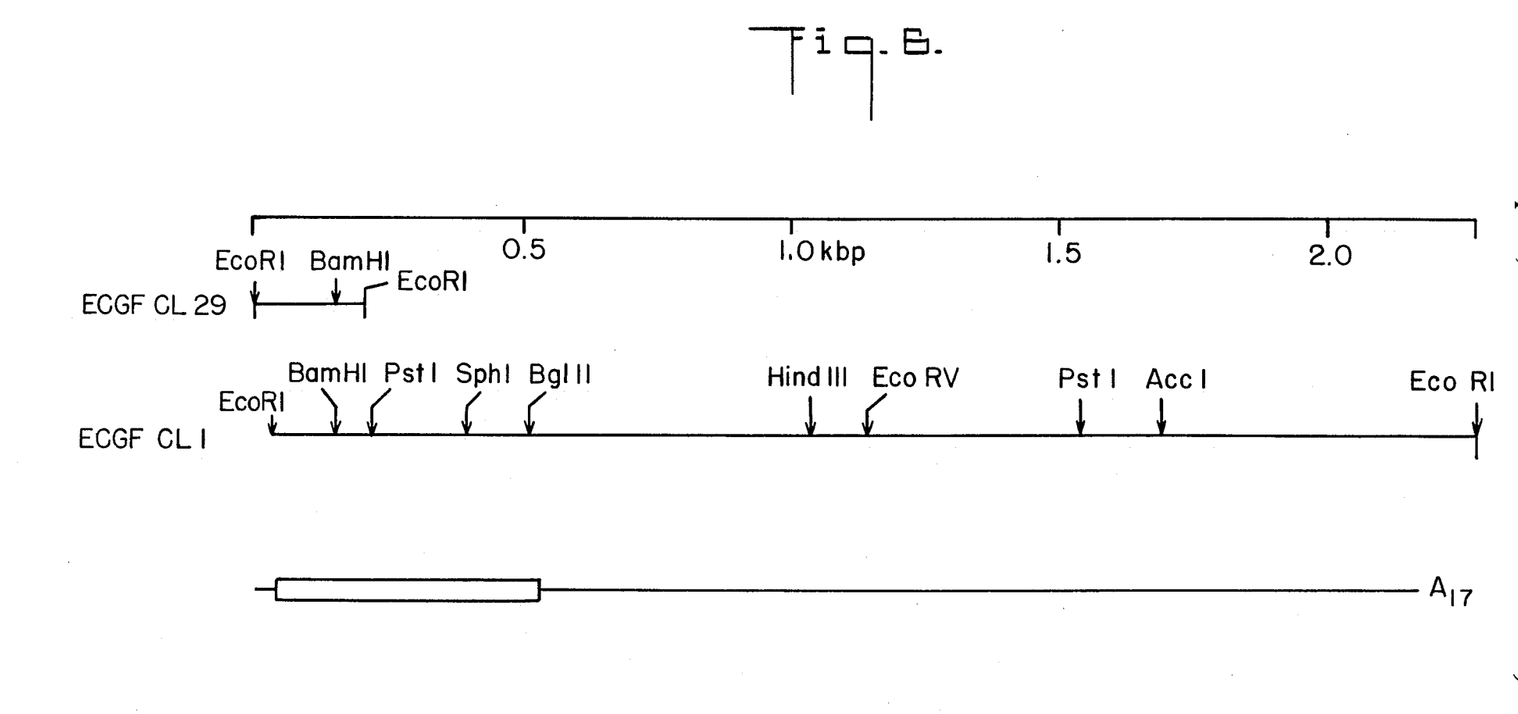
FIG. 6 illustrates a schematic diagram of human ECGF cDNA clones 1 and 29. The open reading box represents the open reading frame encoding human beta ECGF. The EcoRI sites correspond t synthetic oligonucleotide linkers used in the construction of the cDNA library. The poly (A) tail at the 3' end of clone 1 is shown by Al$_7$.

The two clones that were isolated, ECGF clones 1 and 29, were analyzed in further detail. Upon digestion with EcoRI, clone 1 and 29 revealed cDNA inserts of 2.2 and 0.3 Kb, respectively. Nick translation of cloned cDNA and its subsequent use as a radiolabeled probe in Southern blot analysis (Maniatis, et al., supra) revealed that clones 1 and 29 were related and overlapping clones. The overlapping nature of these two clones is shown in FIG. 6.

Figure 7:
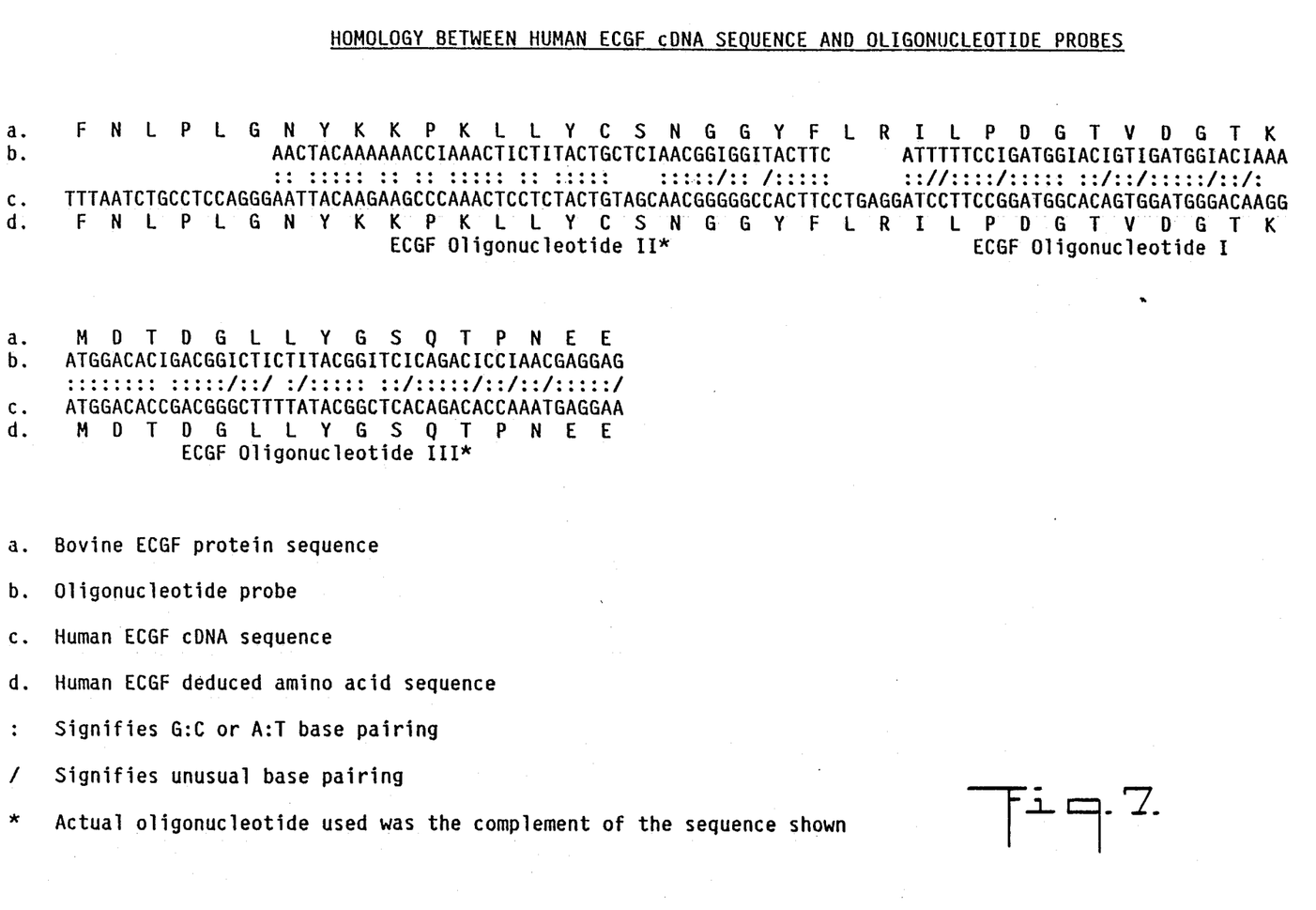
FIG. 7 illustrates homology between human ECGF cDNA sequence and oligonucleotide probes.

Clones 1 and 29 were analyzed in further detail as follows: An additional two oligonucleotides were designed, based upon the amino acid sequence of bovine ECGF. These oligonucleotides were designed based upon the same considerations as those used in the design of the oligonucleotide used to isolate clones 1 and 29. These oligonucleotides (ECGF oligonucleotides II and III) are shown in FIG. 7. These two oligonucleotides as well as oligo(dT)$_{18}$ were radioactively labeled in a kination reaction as described above and used as hybridization probes in Southern blotting experiments. The results of these experiments showed that the 0.3 Kb cDNA insert of clone 29 hybridized to ECGF oligonucleotides I and II but not to ECGF oligonucleotide III or oligo(dT)$_{18}$; the 2.2 Kb cDNA insert of clone 1 hybridized to oligonucleotide I, II, III as well as oligo(dT)$_{18}$. These data and subsequent nucleotide sequence determination of clones 1 and 29 showed that the 3' end of clone 1 ends with a poly(A) tail. Hybridization of clone 1 to ECGF oligonucleotide III, which is based on a cyanogen bromide cleavage product of bovine ECGF, as well as to oligo(dT)$_{18}$, strongly suggested that this clone contains the rest of the coding sequence for both alpha and beta ECGFs as well as a large (greater than 1 Kb) 3' flanking sequence.

The cDNA inserts from clones 1 and 29 were isolated, subcloned into M13mp18, and the ECGF-encoding open reading frame and flanking regions sequenced by the chain termination method [Sanger et al., Proc. Natl. Acad. Sci. USA 74:5463–5467 (1977)]. The nucleotide sequence of these clones and the amino acid sequence deduced from the nucleic acid sequence is shown in FIG. 8. Examination of the nucleotide sequence reveals an open reading frame of 465 nucleotides encoding human ECGF. The 155 amino acids of human ECGF were found to be flanked by translation stop codons. The NH$_2$-terminal amino acid of human beta ECGF deduced from the cDNA sequence is methionine, which most likely serves as the translation initiation residue. These data, together with the relatively non-hydrophobic nature of the first 15–20 amino terminal residues, strongly suggest that human beta ECGF is synthesized without a NH$_2$-terminal signal peptide. A comparison of FIGS. 3 and 8 shows that the amino terminal amino acid sequence of trypsin-cleaved bovine beta ECGF as well as that of bovine alpha ECGF are nearly identical to the amino acid sequence predicted from the nucleotide sequence of lambda ECGF clones 1 and 29. An overall homology between the two species of over 95% is observed.

Figure 9:
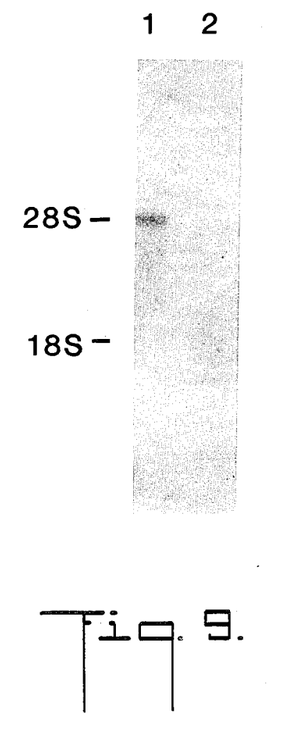

Northern blot analysis (Maniatis, et al, supra) reveals that ECGF mRNA is a single molecular species which comigrates with 28S rRNA (FIG. 9). Considering the variation in the estimated size of 28S rRNA, the approximate size of ECGF mRNA is $4.8 \pm 1.4$ Kb. All of the sequence encoding the mature forms of both alpha and beta ECGF is encoded within ECGF clones 1 and 29, which together encompasses approximately 2.3 Kb. Thus, these data demonstrate that the region 5' and flanking the ECGF-encoding sequences, is very large (approximately $2.5 \pm 1.4$ Kb).

cDNA inserts from clone 1 and clone 29 were excised by digestion with EcoRI and subcloned in pUC8 at the EcoRI site. The plasmid formed from clone 1 was designated pDH15 and the plasmid formed from clone 29 was designated pDH14. The plasmids were deposited in American Type Culture Collection, 12301 Parklawn Drive, Rockville, MD 20852. The plasmid from clone 1, pDH15, was designated ATCC 53336 and the plasmid from clone 29, pDH 14, was designated ATCC 53335.

Thus, this example describes experimental procedures which provide human endothelial cell growth factor essentially free of other proteins of human origin.

ECGF has utility in the growth and amplification of endothelial cells in culture. Currently, ECGF for cell culture use is extracted from bovine brain by the protocol of Maciag, et al., [Proc. Natl. Acad. Sci., 76:11, 5674–5678 (1978)]. This crude bovine ECGF is mitogenic for human umbilical vein endothelial cells [Maciag, et al., J. Biol. Chem 257:5333–5336 (1982)] and endothelial cells from other species. Utilization of heparin with ECGF and a fibronectin matrix permits the establishment of stable endothelial cell clones. The recommended concentration of this crude bovine ECGF for use as a mitogen in vitro is 150 micrograms per milliliter of growth medium.

Recombinant DNA-derived human ECGF has utility, therefore, as an improved substitute for crude bovine ECGF in the in vitro culturing of human endothelial cells and other mesenchymal cells for research use. The activity of human ECGF is expected to be the same as or better than bovine ECGF in the potentiation of endothelial cell growth due to the high degree of homology in the amino acid sequences of both proteins. The expected effective dose range for potentiating cell division and growth in vitro is 5–10 ng of purified ECGF per milliliter of culture medium. Production of the ECGF via recombinant-DNA technologies as outlined in this patent application and subsequent purification as described by Burgess, et al., [J. Biol. Chem. 260:11389–11392 (1985)] will provide large quantities of a pure product of human origin (heretofore unavailable in any quantity or purity) with which to develop models of human homeostatis and angiogenesis.

Recombinant DNA-derived human ECGF also has utility in the potentiation of cell growth on a prosthetic device, rather than a tissue culture flask or bottle. This device may or may not be coated with other molecules which would facilitate the attachment of endothelial cells to the device. These facilitating molecules may include extracellular matrix proteins (e.g. fibronectin, laminin, or one of the collagens), human serum albumin, heperin or other glycosaminoclycans or inert organic molecules. Endothelial cells would be cultured on these surfaces using effective doses of ECGF in the culture medium, ultimately covering the device with an endothelial cell monolayer. This device would then provide a non-thrombogenic surface on the prosthetic device, thus reducing the risk of potentially life-threatening thrombogenic events subsequent to implantation of the prosthetic device.

ECGF has utility in diagnostic applications. Schreiber, et al., [*Proc. Natl. Acad. Sci.* 82:6138 (1985)] developed a double antibody immunoassay for bovine ECGF. In this assay, 96-well polyvinyl chloride plates were coated with rabbit anti-ECGF and the remaining binding sites subsequently blocked with 10% normal rabbit serum. Samples of ECGF were then added to the wells and incubated. After washing, murine monoclonal anti-ECGF was added. After incubation and several washes, rabbit anti-mouse IgG coupled with peroxidase was added. The reaction product was quantitated spectrophotometrically after conversion of 0-phenylenediamine in the presence of hydrogen peroxide. A similarly constructed immunoassay may be useful for monitoring human ECGF levels in disease states affecting endothelial cell growth. Purified recombinant-DNA derived ECGF would be useful as a standard reagent in quantifying unknown ECGF samples.

ECGF also may have potential in the treatment of damaged or in the regeneration of blood vessels and other endothelial cell-lined structures.

It should be appreciated that the present invention is not to be construed as being limited by the illustrative embodiment. It is possible to produce still other embodiments without departing from the inventive concepts herein disclosed. Such embodiments are within the ability of those skilled in the art.

What is claimed is:

1. A process for producing a human endothelial cell mitogenic protein comprising, providing a replicable DNA expression vector capable of expressing a DNA sequence encoding human endothelial cell growth factor in a suitable host, transforming said host to obtain a recombinant host, and maintaining said recombinant host under conditions permitting expression of said DNA sequences to produce endothelial cell growth factor.

2. The process according to claim 1 wherein recovering said endothelial cell growth factor comprises reaction of the proteins expressed by the recombinant host system with a reagent composition comprising at least one binding protein specific for endothelial cell growth factor.

3. An isolated DNA sequence consisting essentially of a DNA sequence encoding human beta endothelial cell growth factor including an initiation codon positioned upstream and adjacent to the codon encoding the NH2-terminal amino acid of naturally occurring human beta endothelial cell growth factor.

4. An isolated DNA sequence encoding a human endothelial cell mitogenic protein, consisting essentially of an initiation codon positioned upstream and adjacent to an open reading frame consisting essentially of a DNA sequence encoding human alpha endothelial cell growth factor.

5. An isolated DNA sequence according to claim 4 wherein the 5'-terminus of said open reading frame begins with 5'-AAT TAC AAG CCC AAA CTC CTC TAC or an equivalent codon series.

6. An isolated DNA sequence according to claim 4 wherein the 5'-terminus of said open reading frame begins with 5'-TTT AAT CTG CCT GGG AAT TAC or an equivalent codon series.

7. A vector comprising a DNA sequence according to claim 4, 5 or 6.

8. A recombinant host microorganism including the plasmid comprising a DNA sequence to claim 4, 5 or 6.

9. A recombinant host microorganism containing a DNA expression vector comprising a DNA sequence consisting essentially of a DNA sequence encoding alpha endothelial cell growth factor and capable of expressing said factor.

10. A replicable DNA expression vector capable of expressing a DNA sequence according to claim 4 or 5 in a self-replicating recombinant system.

11. The self-replicating recombinant system transformed with the vector of claim 10.

12. The recombinant system according to claim 11 wherein said system is in a cell.

13. The recombinant system according to claim 11 wherein said system is cell-free.

14. The recombinant system according to claim 11 obtained by transforming or infecting a member of the group consisting of an *E. coli, B. subtilis,* insect, yeast and vertebrate cell.

15. The recombinant system according to claim 11 obtained by transforming eukaryotes.

16. A cDNA clone comprising a DNA sequence coding alpha human endothelial cell growth factor.

17. A cDNA clone according to claim 16 containing untranslated nucleotide sequences located 3, to the coding sequence for human alpha endothelial cell growth factor as defined by the human beta endothelial cell growth factor mRNA.

18. A process according to claim 1 wherein said growth factor is human alpha endothelial cell growth factor.

19. A process according to claim 1 wherein said growth factor is human beta endothelial cell growth factor.

20. A process for producing a purified human endothelial cell mitogenic protein comprising maintaining a recombinant host microorganism, which includes a plasmid capable of expressing the open reading frame of the DNA sequence according to claim 4, under conditions such that said microorganism produces said mitogenic protein, and isolating said protein.

21. A process according to claim 20 wherein the 5,-terminus of said open reading frame begins with 5'-AAT TAC AAG AAG CCC AAA CTC CTC TAC or an equivalent codon series.

22. A process according to claim 21 wherein said isolation comprises eluting a column formed from crude protein derived from said microorganism with hydrated heparin-Sepharose and collecting said protein in purified form.

* * * * *

UNITED STATES PATENT AND TRADEMARK OFFICE
CERTIFICATE OF CORRECTION

PATENT NO. : 4,868,113

DATED : September 19, 1989

INVENTOR(S) : Michael Jaye; Wilson Burgess; Thomas Maciag; William Drohan

It is certified that error appears in the above-identified patent and that said Letters Patent is hereby corrected as shown below:

Column 1, line 17, "in vitro" should read -- *in vitro* --; line 29, "supra" should read -- *supra* --; line 31, "Proc. Nat'l. Acad. Sci., 2:6138-6142 (1985)]" should read -- Proc. Nat'l. Acad. Sci. USA 82:6138-6142 (1985)] --; line 41, "ECG" should read -- ECGF --; line 46, "supra" should read -- *supra* --; line 48, "supra" should read -- *supra* --.

Column 2, line 9, "poly-merase" should read -- polymerase --; line 40, "8:16-18 (1980)," should read -- 68:16-18 (1980), --.

Column 3, line 7, "supra" should read -- *supra* --.

Column 4, line 24, "t" should read -- to --; line 27, "Al$_7$." should read -- A$_{17}$. --; line 56, "$^{32}$p-labeled" should read -- $^{32}$P-labeled --; line 59, "(200 ug/ml)," should read -- (200 µg/ml) --; line 65, "10 ug human" should read -- 10 µg human --; line 66, "10 ug human" should read -- 10 µg human --.

Column 5, line 9, "in vitro" should read -- *in vitro* --; line 33, "supra" should read -- *supra* --; line 39, "B" should read -- β --; line 45, "B" should read -- β --.
Column 6, line 7, "B" should read -- β --;
Column 6, line 52, "Nat'l. Acad. Sci. 80:" should read -- Nat'l. Acad. Sci. USA 80: --.

Column 7, line 30, "by" should read -- for --; line 45, "supra" should read -- *supra* --.

Column 8, line 12, "supra" should read -- *supra* --; line 30, "supra" should read -- *supra* --; line 68, "supra" should read -- *supra* --.

UNITED STATES PATENT AND TRADEMARK OFFICE
CERTIFICATE OF CORRECTION

PATENT NO. : 4,868,113

DATED : September 19, 1989

INVENTOR(S) : Michael Jaye; Wilson Burgess; Thomas Maciag; William Drohan

It is certified that error appears in the above-identified patent and that said Letters Patent is hereby corrected as shown below:

Column 9, line 2, "Sephadex" should read -- SEPHADEX --; line 13, "Sephadex" should read -- SEPHADEX --; line 18, "supra" should read -- supra --; line 19, "Sephadex" should read -- SEPHADEX --; line 21, "supra" should read -- supra --; line 23, "supra" should read -- supra --; line 35, "(proC.::Tn5)" should read -- (proC::Tn5) --; line 36, "supra" should read -- supra --; line 38, "supra" should read -- supra --; line 42, "(proC.::Tn5)" should read -- (proC::Tn5) --; line 50, "proA$\Delta$ lon" should read -- proA $\Delta$lon --; line 60, "supra" should read -- supra --; line 63, "invacuo" should read -- in vacuo --.

Column 10, line 16, "Prac. Nat'l. Acad. Sci." should read -- Proc. Nat'l. Acad. Sci. USA --; line 26, "then" should read -- than --; line 61, "supra" should read -- supra --; line 68, "32P-labeled" should read -- $^{32}$P-labeled --.

Column 11, line 1, "ours" should read -- hours --; line 15, "supra" should read -- supra --; line 47, "Proc" should read -- Proc. --; line 48, "Nat'l. Acad. Sci. USA" should read -- Nat'l. Acad. Sci. USA --.

Column 12, line 1, "supra" should read -- supra --; line 27, "Proc. Nat'l. Acad. Sci.," should read -- Proc. Nat'l. Acad. Sci. USA --; line 30, "J. Biol. Chem." should read -- J. Biol. Chem. --; line 35, "in vitro" should read -- in vitro --; line 39, "in vitro" should read -- in vitro --; line 46, "in vitro" should read -- in vitro --; line 50, "J. Biol. Chem." should read -- J. Biol. Chem. --.

Column 13, line 5, "Proc. Nat'l. Acad. Sci." should read -- Proc. Nat'l. Acad. Sci. USA --.

UNITED STATES PATENT AND TRADEMARK OFFICE
CERTIFICATE OF CORRECTION

PATENT NO. : 4,868,113

DATED : September 19, 1989

INVENTOR(S) : Michael Jaye; Wilson Burgess; Thomas Maciag; William Drohan

It is certified that error appears in the above-identified patent and that said Letters Patent is hereby corrected as shown below:

In Claim 3, Column 13, line 51, "NH2-terminal" should read -- $NH_2$-terminal --.

In Claim 5, Column 14, line 1, "5'-AAT TAC AAG CCC AAA CTC CTC" should read -- 5' AAT TAC AAG AAG CCC AAA CTC CTC --.

In Claim 6, Column 14, line 5, "5'-TTT AAT CTG CCT GGG AAT TAC" should read -- 5' TTT AAT CTG CCT CCA GGG AAT TAC --.

Signed and Sealed this

Twentieth Day of August, 1991

Attest:

HARRY F. MANBECK, JR.

*Attesting Officer*   Commissioner of Patents and Trademarks